United States Patent [19]

Pifferi

[11] 4,005,082
[45] Jan. 25, 1977

[54] 1H-2,3-BENZOXAZINES
[75] Inventor: Giorgio Pifferi, Milan, Italy
[73] Assignee: Gruppo Lepetit S.p.A., Milan, Italy
[22] Filed: Mar. 19, 1971
[21] Appl. No.: 126,357

Related U.S. Application Data

[63] Continuation-in-part of Ser. No. 761,835, Sept. 23, 1968, abandoned.

[30] Foreign Application Priority Data

Sept. 25, 1967 United Kingdom .............. 43621/67

[52] U.S. Cl. ...................... 260/244 R; 424/248.4; 260/240 G
[51] Int. Cl.$^2$ ...................................... C07D 265/20
[58] Field of Search ............... 260/244 R

[56] References Cited

UNITED STATES PATENTS

| | | | |
|---|---|---|---|
| 2,650,919 | 9/1953 | Cusic | 260/244 R |
| 3,058,980 | 10/1962 | Berg | 260/244 R |
| 3,417,085 | 12/1968 | Kuch et al. | 260/244 R |
| 3,418,317 | 12/1968 | Pifferi et al. | 260/244 R |
| 3,476,752 | 11/1969 | Pifferi et al. | 260/244 R |

FOREIGN PATENTS OR APPLICATIONS

| | | | |
|---|---|---|---|
| 1,598,168 | 7/1970 | France | 260/244 R |
| 6,813,657 | 3/1969 | Netherlands | 260/244 R |

OTHER PUBLICATIONS

Migrdichian Organic Synthesis, vol. 1, pp. 465–468, N.Y., Reinhold, 1957.
Fieser, et al., Organic Chemistry pp. 218–219, Boston, Heath, 1944.
Noller Chemistry of Organic Compounds 2nd Ed. p. 211, Philadelphia, Saunderv, 1957.
Shriner, et al., The Systematic Identification of Organic Compounds 3rd. Ed. pp. 167–171, N.Y., Wiley, 1948.
Pifferi, et al., III Chem. Abst. vol. 73, No. 77261a (1970).
Pifferi, et al., IV Ann. Chim. (Rome) vol. 59, pp. 1136–1151 (1969).
Degering An Outline of Organic Nitrogen Compounds, p. 384, Ypsilanti, Mich. University Lithoprinters, 1950.
Migrdichian Organic Synthesis, vol. 1, p. 151, N.Y., Reinhold, 1957.
Wagner, et al., Synthetic Organic Chemistry, pp. 728–729, N.Y., Wiley, 1953.

*Primary Examiner*—Natalie Trousof
*Attorney, Agent, or Firm*—Joseph Hirschmann

[57] ABSTRACT

4-Substituted-1H-2,3-benzoxazines with a chlorine atom linked to the benzene ring, and a process for their preparation, are described. The compounds are administered as sedative, hypnotic and tranquillizing agents.

2 Claims, No Drawings

1H-2,3-BENZOXAZINES

This application is a continuation-in-part of our co-pending application Ser. No. 761,835 filed Sept. 23, 1968 now abandoned.

This invention relates to a new class of compounds and to a method for preparing them.

More particularly, the compounds with which the invention is concerned are represented by the formula

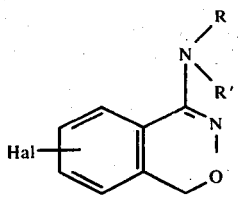

wherein Hal stands for halogen, preferably chlorine, R is a member of the class consisting of hydrogen and lower alkyl, R' is a member of the class consisting of hydrogen, lower alkyl, di-lower alkylamino-lower alkyl, optionally substituted aryl, the group -NHR'' wherein R'' is hydrogen or lower alkyl, the group -NR''', wherein R''' is an optionally substituted lower alkylidene, or R and R' taken together with the nitrogen atom form a heterocyclic ring.

The process consists in heating at a temperature between 70° and 150° C a mixture of a 4-halogen-1H-2,3-benzoxazine of the formula

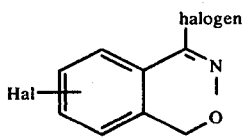

and a compound of the formula

NHRY wherein R has the above significance and Y represents the same groups as R' except for the radical —NR'''. Although the reaction usually takes place with about equimolecular amounts of the two reactants, it is preferred to use a more or less important excess of the second reactant, i.e. of NHRY. According to the nature of the starting compounds it may be sometimes convenient to dissolve them in a small quantity of an organic solvent, such as a lower alkanol; in this case the reaction temperature is the reflux temperature of the mixture.

The time necessary for the reaction to be completed is generally between about 0.5 and 6 hours, and all the products are usually obtained in good yields.

The compounds obtained according to the above described reaction, bearing a 2-unsubstituted hydrazino group at position 4 of the heterocyclic ring, can, if desired, be converted into the corresponding hydrazones, by contacting them with an at least equimolecular amount of a carbonylic compound.

The reaction is carried out in a solution of an organic solvent, but also the carbonyl compound can in some cases, dependently on its nature, act as the solvent.

The above outlined process is the preferred one. Other obvious variants are workable and are within the usual skillfulness of an average technician.

The compounds of the invention have interesting pharmacological properties as CNS depressant agents. The compounds are administered as sedative, hypnotic and tranquilizing agents.

For instance 4-(1-methyl-hydrazino)-6-chloro-1H-2,3-benzoxazine decreases remarkably the spontaneous activity in mice at the dose of 10 mg/Kg i.p. Further the activity of the compound on the secondary conditioned avoidance response in rats is already apparent at dose levels of 15 mg/Kg i.p. and 30 mg/Kg orally; inhibition of the primary conditioned avoidance response is produced by doses of 30 mg/Kg i.p. and 60 mg/Kg orally.

The toxicity data are also favourable, since the $LD_{50}$ in mice was found to be 323.0 mg/Kg intraperitoneally and 452.0 orally.

Still more active is the 4-(1-methylhydrazino)-7-chloro-1H-2,3-benzoxazine, for which the corresponding data were found to be the following: spontaneous activity in mice, 6 mg/kg. i.p.; secondary conditioned avoidance response in rats 10 mg/kg, i.p.; primary conditioned avoidance response in rats 30 mg/kg i.p.; $LD_{50}$ in mice 300 mg/kg i.p.

Comparable data were obtained for a number of other compounds of this class, some of which show a still lower toxicity as compared with the above considered benzoxazine. For instance, the $LD_{50}$ for 6-chloro-4-(2-ethylidene-1-methylhydrazino)-1H-2,3-benzoxazine is about 700 mg/Kg i.p. and over 1000 mg/Kg orally.

The compounds may be used in pharmaceutical compositions, like tablets and ampoules for injection, at doses of 10–100 mg. orally, and of 10–40 mg. i.v. or i.m.

The following non limitative examples illustrate the invention.

EXAMPLE 1

Preparation of 6-chloro-4-methylamino-1H-2,3-benzoxazine.

An amount of 3 g. of 4,6-dichloro-1H-2,3-benzoxazine is heated for 4 hours in a sealet tube at 120° C with 25 g. of monomethylamine.

The mixture is allowed to cool then taken up with diethyl ether and extracted with hydrochloric acid.

The ether layer is discarded, and the aqueous solution is made alkaline with a 30% sodium hydroxide solution then the mixture is extracted with diethyl ether. The ether extracts are washed with water, dried over anhydrous sodium sulphate, and distilled in vacuo. The residue is crystallized from ethyl acetate, thus obtaining 2.4 g. of 6-chloro-4-methylamino-1H-2,3-benzoxazine. Yield 82%, m.p. 147.5–5–149° C.

Analysis

| | | |
|---|---|---|
| Calcd. for $C_9H_9ClN_2O$ | C,55.00; H,4.58; | N,14.24; Cl,18.03 |
| Found | C,55.29; H,4.70; | N,13.62; Cl,17.84 |

EXAMPLE 2

Preparation of 6-chloro-4-dimethylamino-1H-2,3-benzoxazine

An amount of 1 g. of 4,6-dichloro-1H-2,3-benzoxazine is heated for 4 hours in a sealed tube at 120° C with 25 ml. of dimethylamine. The mixture is allowed to cool, then is poured into a glass container, rinsing the tube with water and diethyl ether.

The mixture is extracted with hydrochloric acid, and the organic phase is discarded. The aqueous layer is made alkaline with a 30% sodium hydroxide solution, and the solution is extracted several times with diethyl ether. The combined ether extracts are washed with water, dried over anhydrous sodium sulphate, and distilled in vacuo. The residue is crystallized from diisopropyl ether thus obtaining 0.75 g. of 6-chloro-4-dimethylamino-1H-2,3-benzoxazine. Yield 72% m.p. 88°–88.5° C.

Analysis

| | |
|---|---|
| Calcd. for $C_{10}H_{11}ClN_2O$ | C,57.02; H,5.20; N,13.30; Cl,16.84 |
| Found | C,57.20; H,5.04; N,13.38; Cl,17.00 |

EXAMPLE 3

Preparation of 6-chloro-4-hydrazino-1H-2,3-benzoxazine

An amount of 3.6 g. of 4,6-dichloro-1H-2,3-benzoxazine and 1.8 ml. of anhydrous hydrazine are dissolved in 18 ml. of absolute ethanol and refluxed for 30 minutes. The mixture is allowed to cool, then is distilled in vacuo. The residue is taken up with methylene chloride and filtered from precipitated hydrazine hydrochloride. The filtered solution is distilled to dryness and the residue crystallized from ethanol. An amount of 2.10 g. of 6-chloro-4-hydrazino-1H-2,3-benzoxazine is obtained. Yield 60% m.p. 148°–149° C.

Analysis

| | |
|---|---|
| Calcd. for $C_8H_8ClN_3O$ | C,48.63; H,4.05; N,21.27; Cl,17.95 |
| Found | C,48.81; H,4.28; N,21.50; Cl,18.21 |

EXAMPLE 4

Preparation of 6-chloro-4-(1-methylhydrazino)-1H-2,3-benzoxazine

To 2.52 g of 4,6-dichloro-1H-2,3-benzoxazine dissolved in 13 ml. of absolute ethanol, 1.73 g. of methylhydrazine are added. The mixture is refluxed for 30 minutes, allowed to cool and then is distilled in vacuo. The residue is taken up with diethyl ether and the solution is filtered from any insoluble. The filtered solution is distilled to dryness, and the residue taken up with 10 ml of diisopropyl ether. After cooling on ice for 0.5 hours, the mixture is filtered and the collected solid crystallized from ethyl acetate, thus obtaining 2.0 g. of 6-chloro-4-(1-methylhydrazino)-1H-2,3-benzoxazine. Yeild 65%; m.p. 124°–125° C.

Analysis

| | |
|---|---|
| Calcd. for $C_9H_{10}ClN_3O$ | C,51.10; H,4.77; N,19.87; Cl, 16.76 |
| Found | C, 50.82; H,4.72; N,19.65; Cl,16.90 |

EXAMPLE 5

Preparation of 6-chloro-4-(isopropylidene-hydrazino)-1H-2,3-benzoxazine

An amount of 0.15 g. of 6-chloro-4-hydrazino-1H-2,3-benzoxazine is dissolved in 15 ml. of anhydrous acetone, by moderate heating. The solution is allowed to stand for 1 hour, then the solvent is removed in vacuo at room temperature. The residue is taken up with hexane and allowed to stand two days. After filtering, the solution is concentrated to dryness in vacuo and the residue recrystallized from the same solvent. Yield 0.1 g. of 6-chloro-4-(isopropylidene-hydrazino)-1H-2,3-benzoxazine (55%); m.p. 76°–77° C.

Analysis

| | |
|---|---|
| Calcd. for $C_{11}H_{12}ClN_3O$ | C,55.60; H,5.09; N,17.68; Cl,14.92 |
| Found | C,55.79; H,4.88; N,17.60; Cl,14.75 |

EXAMPLE 6

Preparation of 6-chloro-4-(2-isopropylidene-1-methylhydrazino)-1H-2,3-benzoxazine An amount of 0.5 g. of 6-chloro-4-(1-methylhydrazino)-1H-2,3-benzoxazine is dissolved in 25 ml. of anhydrous acetone at room temperature. The mixture is allowed to stand for 1 hour, then the solvent is removed in vacuo at room temperature. The residue is extracted repeatedly with warm hexane, using in all 50 ml. of the solvent. The solid is discarded and the solution is evaporated to dryness in vacuo. The residue is recrystallized from diisopropyl ether, to give 0.25 g. (42%) of 6-chloro-4-(2-isopropylidene-1-methylhydrazino)-1H-2,3-benzoxazine; m.p. 105°–106° C. Analysis

| | |
|---|---|
| Calcd. for $C_{12}H_{14}ClN_3O$ | C,57.25; H,5.61; N 16.70; Cl,14.09 |
| Found | C,57.22; H,5.59; N,16.50; Cl,13.85 |

EXAMPLE 7

Preparation of 6-chloro-4-[1-methyl-2-(4-nitro-benzylidene)-hydrazino]-1H-2,3-benzoxazine An amount of 1.4 g. of 6-chloro-4-(1-methylhydrazino)-1H-2,3-benzoxazine is dissolved in 70 ml. of ethanol by heating at 50° C, then 1.12 g. of p-nitro-benzaldehyde are added. The solution is stirred, then allowed to stand for 2 hours. The formed crystals are collected by filtering and recrystallized from 500 ml. of benzene. An amount of 1.7 g. (74%) of 6-chloro-4-[1-methyl-2-(4-nitro-benzylidene)-hydrazino]-1H-2,3-benzoxazine are obtained; m.p. 251° C with decomposition.

Analysis

| | | |
|---|---|---|
| Calcd. for C$_{16}$H$_{13}$ClN$_4$O$_3$ | C,55.77; H,3.80; N,16.25; Cl,10.28 | |
| Found | C,55.80; H,4.03; N,16.12; Cl, 9.85 | |

EXAMPLE 8

Preparation of 6-chloro-4-(2-ethylidene-1-methylhydrazino)-1H-2,3-benzoxazine

To a solution of 3 g. of 6-chloro-4-(1-methylhydrazino)-1H-2,3-benzoxazine in 180 ml. of anhydrous benzene 1 g. of acetaldehyde in 30 ml. of anhydrous benzene is added. The mixture is allowed to stand for 2 hours, then the solvent is distilled off in vacuo and the residue recrystallized from isopropyl ether. Yield 2.4 g. (71.2%) of 6-chloro-4-(2-ethylidene-1-methylhydrazino)-1H-2,3-benzoxazine; m.p. 111°–112° C.

Analysis

| | |
|---|---|
| Calculated for C$_{11}$H$_{12}$ClN$_3$O | C,55.60; H,5.08; N,17.69; Cl,14.92 |
| Found | C,56.00; H,5.21; N,17.50; Cl,15.00 |

EXAMPLE 9 TO 15

The following compounds are prepared by substantially the same process as is described in Example 8 from the corresponding starting compounds:

| | Compound | Yield % | M.p. ° C |
|---|---|---|---|
| 9. | 6-chloro-4-(1-methyl-2-propylidenehydrazino)-1H-2,3-benzoxazine | 79.0% | 66–67° |
| 10. | 6-chloro-4-(2-p-chlorobenzylidene-1-methylhydrazino)-1H-2,3-benzoxazine | 76.0% | 225° |
| 11. | 6-chloro-4-(1-ethyl-2-p-nitrobenzylidenehydrazino)-1H-2,3-benzoxazine | 81.3% | 184° dec. |
| 12. | 7-chloro-4-methylamino-1H-2,3-benzoxazine | 68.7% | 137–138° |
| 13. | 7-chloro-4-dimethylamino-1H-2,3-benzoxazine | 74.1% | 72–73° |
| 14. | 7-chloro-4-hydrazino-1H-2,3-benzoxazine | 70.0% | 179–180° dec. (hydrochloride) |
| 15. | 7-chloro-4-(1-methylhydrazino)-1H-2,3-benzoxazine | 81.2% | 191–192° dec. (hydrochloride) |

We claim:
1. 6-Chloro-4-(isopropylidene-hydrazino)-1H-2.3-benzoxazine.
2. 6-Chloro-4-(2-isopropylidene-1-methylhydrazino)-1H-2.3-benzoxazine.

* * * * *